(12) United States Patent
Jupe et al.

(10) Patent No.: US 7,094,538 B2
(45) Date of Patent: Aug. 22, 2006

(54) DIAGNOSTIC ASSAY FOR CANCER SUSCEPTIBILITY

(75) Inventors: Eldon R. Jupe, Norman, OK (US); Linda F. Thompson, Oklahoma City, OK (US); Regina Resta, Slingersland, NY (US); Robert T. Dell'Orco, Gaithersburg, MD (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 450 days.

(21) Appl. No.: 10/166,218

(22) Filed: Jun. 10, 2002

(65) Prior Publication Data

US 2003/0073107 A1    Apr. 17, 2003

Related U.S. Application Data

(63) Continuation of application No. 09/530,976, filed on May 5, 2000, now abandoned, which is a continuation of application No. PCT/US98/23686, filed on Nov. 6, 1998.

(60) Provisional application No. 60/064,880, filed on Nov. 6, 1997.

(51) Int. Cl.
  *C12Q 1/68*    (2006.01)
  *C12P 19/34*   (2006.01)
  *C07H 21/00*   (2006.01)
  *C07H 21/02*   (2006.01)
  *C07H 21/04*   (2006.01)

(52) U.S. Cl. .................... 435/6; 435/91.1; 435/91.5; 536/23.1; 536/23.5; 536/24.31; 536/24.33; 536/25.32

(58) Field of Classification Search ............ 435/6, 435/91.1, 91.2, 91.5, 91.31; 536/23.1, 23.31, 536/23.5, 24.31, 24.33, 25.32, 24.5
See application file for complete search history.

(56) References Cited

U.S. PATENT DOCUMENTS 5,401,635 A    3/1995  Nakamura et al. ............ 435/6
5,776,738 A *  7/1998  Dell'Orco et al. ......... 435/91.2

FOREIGN PATENT DOCUMENTS

| WO | WO 96/05306 | 2/1996 |
| WO | WO 96/40919 | 12/1996 |
| WO | WO 98/20167 | 5/1998 |

OTHER PUBLICATIONS

Bentley et al., "Rapid methods for detection of polymorphic markers in genomic DNA," *Methods in Molecular Biology*, in: *Protocols in Human Molecular Genetics*, 9:51-68, c1991.

Dell'Orco et al., "Differential regulation in prhibitin in prostate cancer cells," *Molec. Biol. Cell*, 7:24a, 1992.

Jupe et al., "Prohibition antiproliferative activity and lack of heterozygosity in immortalized cell lines," *Exp. Cell Res.*, 218:577-580, 1995.

Jupe et al., "Prohibitin in breast cancer cell lines: loss of antiproliferative activity is linked to 3'untranslated region mutations," *Cell Growth and Differentiation*, 7:871-878, 1996.

Jupe et al., "The 3'untranslated region of prohibitin and cellular immortalization," *Exp. Cell Res.*, 224:128-135, 1996.

Liu et al., "Restriction endonuclease fingerprinting (REF): a sensitive method for screening mutations in long, contiguous segements of DNA," *BioTechniques*, 18:470-477, 1995.

Sato et al., "The human prohibitin gene located on chromosome 17q21 is mutated in sporadic breast cancer," *Cancer Res.*, 52:1643-1646, 1992.

* cited by examiner

*Primary Examiner*—Jane Zara
(74) *Attorney, Agent, or Firm*—Fulbright & Jaworski

(57) ABSTRACT

The lifetime probability of a person developing cancer can now be determined based on an allelic variation found in the 3'UTR of the prohibitin gene. The probability is dependent on the sequence of the 3'UTR at position 729, i.e., whether there is a thymine (T) or a cytosine (C) or both at this position. Determining the sequence at the position 729 can be done by any number of standard techniques. Preferably, the sequence is determined by amplifying this region by PCR and subjecting it to an RFLP analysis.

41 Claims, 3 Drawing Sheets

```
  1  CCCAGAAATC ACTGTGAAAT TTCATGATTG GCTTAAAGTG AAGGAAATAA
            P1
 51  AGGTAAAATC ACTTCAGATC TCTAATTAGT CTATCAAATG AAACTCTTTC
101  ATTCTTCTCA CATCCATCTA CTTTTTTATC CACCTCCCTA CCAAAAATTG
151  CCAAGTGCCT ATGCAAACCA GCTTAGGTC  CCAATTCGGG GCCTGCTGGA
201  GTTCCGGCCT GGGCACCAGC ATTTGGCAGC ACGCAGGCGG GGCAGTATGT
251  GATGGACTGG GGAGCACAGG TGTCTGCCTA GATCCACGTG TGGCCTCCGT
301  CCTGTCACTG ATGGAAGGTT TGCGGATGAG GGCATGTGCG GCTGAACTGA
351  GAAGGCAGGC CTCCGTCTTC CAGCGGTTC  CTGTGCAGAT GCTGCTGAAG
401  AGAGGTGCCG GGGAGGGGCA GAGAGGAAGT GGTCTGTCTG TTACCATAAG
451  TCTGATTCTC TTTAACTGTG TGACCAGCGG AAACAGGTGT GTGTGAACTG
501  GGCACAGATT GAAGAATCTG CCCCTGTTGA GGTGGGTGGG CCTGACTGTT
551  GCCCCCAGG  GTCCTAAAAC TTGGATGGAC TTGTATAGTG AGAGAGGAGG
                              P4
601  CCTGGACCGA GATGTGAGTC CTGTTGAAGA CTTCCTCTCT ACCCCCACC
                       P3
651  TTGGTCCCTC TCAGATACCC AGTGGAATTC CAACTTGAAG GATTGCATCC
701  TGCTGGGGCT GAACATGCCT GCCAAGACG  TGTCCGACCT ACGTTCCTGG
751  CCCCCTCGTT CAGAGACTGC CCTTCTCACG GGCTCTATGC CTGCACTGGG
801  AAGGAAACAA ATGTGTATAA ACTGCTGTCA ATAAATGACA CCCAGACCTT
                                                   P2
851  CC
```

FIG. 1

```
   1 AGGACTGGTG GGCAATGTGC TCTGCTTCCC CCCGCTTCCC CCGCTAGCCA
  51 TCAGGAGGAA GTAAACTCCC CGAGTTCCTT CAGGAGCCTG GGAAGGTGGC
 101 TTTCTGGTGA AGGGCCTTTG GTTGTAGCCT GACATGCGGT GCCCTGAGGT
               P1'
 151 TTGATCTTTG TCTCCACCTC CATTCTTTTA GGCTGAGCAA CAGAAAAGG
 201 CGGCCATCAT CTCTGCTGAG GGCGACTCCA AGGCAGCTGA GCTGATTGCC
 251 AACTCACTGG CCACTGCAGG GGATGGCCTG ATCGAGCTGC GCAAGCTGGA
 301 AGCTGCAGAG GACATCGCGT ACCAGCTCTC ACGCTCTCGG AACATCACCT
 351 ACCTGCCAGC GGGGCAGTCC GTGCTCCTCC AGCTGCCCCA GTGAGGGCCC
 401 ACCCTGCCTG CACCTCCGCG GCTGACTGG GCCACAGCCC CGATGATTCT
 451 TAACACAGCC TTCCTTCTGC TCCCACCCA  GAAATCACTG TGAAATTTCA    24
                                  *
 501 TGATTGGCTT AAAGTGAAGG AAATAAAGGT AAAATCACTT CAGATCTCTA    74
 551 ATTAGTCTAT CAAATGAAAC TCTTTCATTC TTCTCACATC CATCTACTTT   124
 601 TTTATCCACC TCCCTACCAA AAATTGCCAA GTGCCTATGC AAACCAGCTT   174
 651 TAGGTCCCAA TTCGGGGCCT GCTGGAGTTC CGGCCTGGGC ACCAGCATTT   224
 701 GGCAGCACGC AGGCGGGGCA GTATGTGATG GACTGGGGAG CACAGGTGTC   274
 751 TGCCTAGATC CACGTGTGGC CTCCGTCCTG TCACTGATGG AAGGTTTGCG   324
               ++++++              P3'
 801 GATGAGGGCA TGTGCGGCTG AACTGAGAAG GCAGGCCTCC GTCTTCCCAG   374
 851 CGGTTCCTGT GCAGATGCTG CTGAAGAGAG GTGCCGGGGA GGGGCAGAGA   424
 901 GGAAGTGGTC TGTCTGTTAC CATAAGTCTG ATTCTCTTTA ACTGTGTGAC   474
 951 CAGCGGAAAC AGGTGTGTGT GAACTGGGCA CAGATTGAAG AATCTGCCCC   524
1001 TGTTGAGGTG GGTGGGCCTG ACTGTTGCCC CCAGGGTCC TAAAACTTGG    574
1051 ATGGACTTGT ATAGTGAGAG AGGAGGCCTG GACCGAGATG TGAGTCCTGT   624
1101 TGAAGACTTC CTCTCTACCC CCACCTTGG TCCCTCTCAG ATACCCAGTG    674
1151 GAATTCCAAC TTGAAGGATT GCATCCTGCT GGGGCTGAAC ATGCCTGCCA   724
                                            P4'
1201 AAGACGTGTC CGACCTACGT TCCTGGCCCC CTCGTTCAGA GACTGCCCTT   774
        *****
1251 CTCACGGGCT CTATGCCTGC ACTGGGAAGG AAACAAATGT GTATAAACTG   824
1301 CTGTCAATAA ATGACACCCA GACCTTCC                          852
               P2
```

DIAGNOSTIC ASSAY FOR CANCER SUSCEPTIBILITY

This is a continuation, of prior application Ser. No. 09/530,976, filed May 5, 2000 now abandoned which is a continuation of PCT/US98/23686 filed Nov. 6, 1998; which is a continuation of 60/064,880 filed Nov. 6, 1997, which is hereby incorporated herein by reference in its entirety. The entire disclosure of the prior application, from which a copy of the oath or declaration is supplied under paragraph 3 below, is considered as being part of the disclosure of the accompanying application, and is hereby incorporated by reference therein.

TECHNICAL FIELD OF THE INVENTION

The invention relates to a diagnostic assay for determining susceptibility to cancer based on the sequence of the 3' untranslated region of the prohibitin gene.

BACKGROUND OF THE INVENTION

While the success of cancer treatment depends greatly on early detection, many types of cancers remain undiagnosed in early stages of the disease. Breast cancer is the second leading cause of cancer-related deaths of women in North America. Prostate cancer is the most common noncutaneous malignant disease among males. The incidence of prostate cancer increases more rapidly with age than any other type of cancer, and it often causes death while remaining undiagnosed. Bladder cancer is potentially curable if treated in the early stages of tumor development, but recurrence rates are high. Ovarian cancer is the most common cause of gynecological cancer death, with most patients diagnosed during the advanced stages of the disease. Lung cancer is the most common cause of cancer deaths, second behind prostate cancer in occurrence for males and third behind breast and colorectal cancers for women.

One area of advancement in early detection of cancers has centered on the identification of mutations in tumor suppressor genes. Tumor suppressor genes have been shown to regulate the development of many types of cancer. For example, abnormal expression of mutated p53 tumor suppressor gene has been demonstrated in breast, prostate, and ovarian carcinoma cell lines and/or tumor samples. Rubin, et al., "Two prostate carcinoma cell lines demonstrate abnormalities in tumor suppressor genes," *J Surg Oncol* 46:1–6 (1991); Munshi, et al., "p53 molecule as a prognostic marker in human malignancies," *J La State Med Soc* 150:175–178 (1998); Suzuki, et al., "Loss of heterozygosity on chromosome 6q27 and p53 mutations in epithelial ovarian cancer," *Med Oncol* 15:119–123 (1998). Germline mutations in both BRCA1 and BRCA2 genes have been found in breast and ovarian cancer patients. Randall, et al., "Germline mutations of the BRCA1 and BRCA2 genes in a breast and ovarian cancer patient," *Gynecol Oncol* 70:432–434 (1998).

The antiproliferative human prohibitin gene, which maps to chromosome 17 at q21 (White, et al., "Assignment of the human prohibitin gene (PHB) to chromosome 17 and identification of a DNA polymorphism," *Genomics* 11:228–230 (1991)) has been examined in association with various types of cancer. In one study, a large number of human tumors of the breast, ovary, liver, and lung were examined for somatic mutations in the prohibitin gene, and although mutations were observed in a few sporadic breast cancers, none were identified in any of the other cancers. Sato, et al., "The human prohibitin (PHB) gene family and its somatic mutations in human tumors," *Genomics* 17:762–764 (1993). Cliby, et al. also demonstrated that the prohibitin gene does not play a role in ovarian carcinogenesis. Cliby, et al., "Absence of prohibitin gene mutations in human epithelial ovarian tumors," *Gynecol Oncol* 50:34–37 (1993). Asamoto and Cohen demonstrated that prohibitin overexpression but not mutation was involved in the early stages of rat bladder carcinogenesis. Asamoto, M. and Cohen, S. M., "Prohibitin gene is overexpressed but not mutated in rat bladder carcinomas and cell lines," *Cancer Lett* 83:201–207 (1994). While prohibitin was an initial candidate gene for a familial breast and ovarian tumor suppressor locus based on a frequent loss of heterozygosity in this region in familial and sporadic breast cancers (Sato, et al., "The human prohibitin gene located on chromosome 17q21 in sporadic breast cancer," *Cancer Res* 52:1634–1646 (1992)), positional cloning studies resulted in the identification of BRCA1 rather than prohibitin as a familial breast cancer gene on chromosome 17 (Miki, et al., "A strong candidate for the breast and ovarian cancer susceptibility gene BRCA1," *Science* 266: 66–71 (1994)). Additional studies did not identify any somatic mutations in the prohibitin protein coding region in familial/hereditary breast cancers suggesting that the protein coding region is not frequently mutated in breast cancers. Sato et al., *Genomics* 17:762–764 (1993).

In WO 96/40919, Dell'Orco et al. identified mutations in the 3' untranslated region (3'UTR) of the prohibitin gene (SEQ ID NO:1) which are diagnostic for increased susceptibility to cancer, particularly breast cancer. Full length prohibitin cDNAs for the BT-20, MCF7 and SK-BR-3 breast cancer cell lines were sequenced, and mutations restricted to the 3' UTR were identified. These three cell lines were also arrested in cell cycle progression when full length prohibitin transcript was introduced by microinjection. All of them were also homozygous for the B-allele. Compared to the sequence of the wild type prohibitin 3' UTR (WT) (SEQ ID NO:1), two point mutations were identified for BT-20: G (guanine) to A (adenine) at position 758 and T (thymine) to C (cytosine) at position 814. MCF7 also had two point mutations: G to A at position 236 and C to T at position 729. SK-BR-3 showed 26 base changes including a change of C to T at position 729. Thus, MCF7 and SK-BR-3 both had a change of C to T at position 729.

In WO 98/20167, Jupe et al. disclosed that, contrary to the teachings of the prior prohibitin work, this change from C to T at position 729 is the result not of a somatic mutation, but rather the result of a natural allelic variation at this point, i.e., it is a germline polymorphism. Furthermore, it is a germline polymorphism that can be used as a susceptibility marker for breast cancer. Carriers of the T-allele (C/T) have an approximately 2-fold increased risk of developing breast cancer. Further, data indicate that the frequency of homozygosity for 729-T appears to be approximately 4–5-fold higher in breast cancer patients than in unaffected females, that 4% of all breast cancers develop in women who are homozygous T/T (which likely make up less than 1% of unaffected women), and that their lifetime risk of developing breast cancer is approximately 50%.

It has now been found that the prohibitin gene, located on chromosome 17q21 near the BRCA1 locus, exhibits a germline polymorphism in the 3'UTR that can be used as a susceptibility marker for other types of cancer.

BRIEF DESCRIPTION OF THE DRAWINGS

FIG. 1 illustrates the 5'-3' sense sequence of the wild type prohibitin 3' UTR and the location of primers (underlined)

Figure 3:
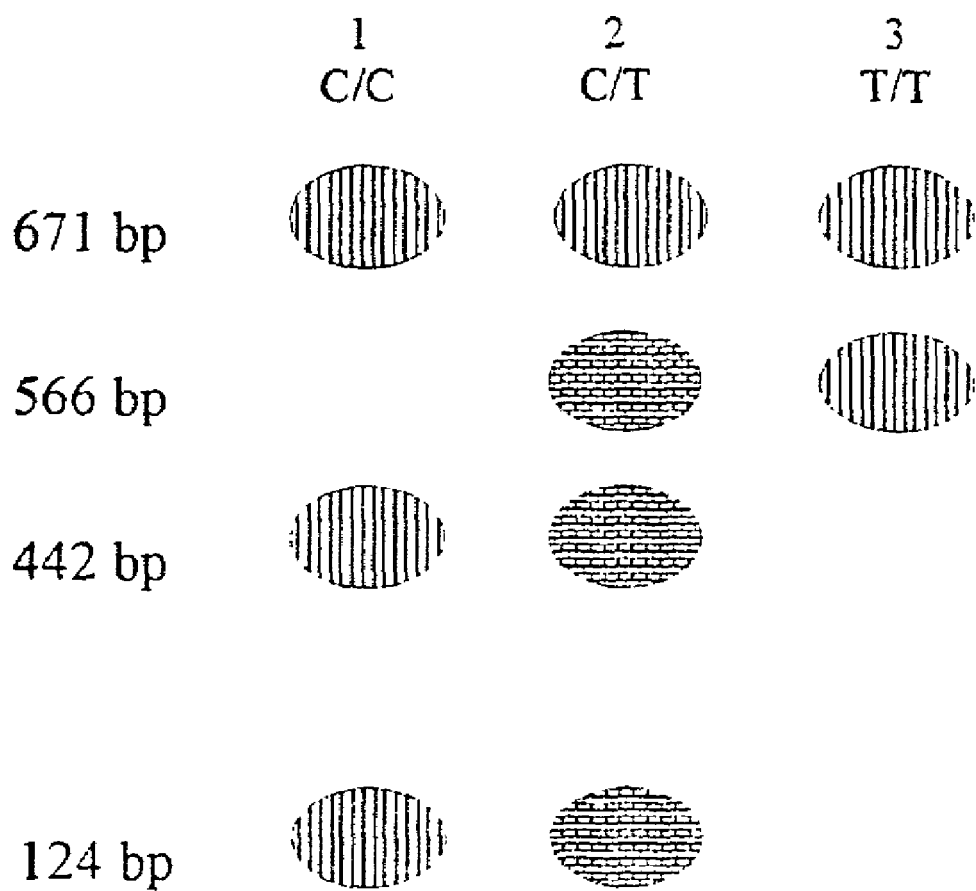

which may be utilized for an AflIII restriction fragment length polymorphism (RFLP) assay for genotyping. The assay is run in two steps with the initial primer set P1/P2 being used for PCR amplification. The initial PCR reaction products are then run on a 2.5% agarose gel and the 852 bp band is excised and purified. The 852 bp fragment is used as the template in PCR with one of the primer sets P3/P2 or P4/P2 to produce a sub-fragment. This subfragment is purified through microspin columns (Pharmacia), and digested with AflIII. Primers P1, P3, and P4 are all sense primers. Primer P2 is an antisense primer whose sequence is 5'-GGAAGGTCTGGGTGTCATTT-3' (SEQ ID NO:2).

FIG. 2 illustrates the 5'-3' sense sequence of the prohibitin gene which begins in intron 6, contains the protein coding region of exon 7 and continues to the end of the 3'UTR. The primers P1' (SEQ ID NO:3) (forward) and P2 (SEQ ID NO:2) (reverse) are used to synthesize the PCR fragment that is used for an AflIII RFLP genotyping assay. The 1237 bp fragment (from position 93 to position 1328 in FIG. 2) that is synthesized is digested with AflIII to determine the genotype. The symbol "*" is below the nucleotide which marks the beginning of the 852 bp 3'UTR coding sequence (FIG. 1), and the numbers on the right of the sequence give the base number for the 852 bp 3'UTR coding sequence. The symbol "++++++" is below the location of the constitutive AflIII site while the symbol "******" is below the location of the polymorphic site. Cleavage by AflIII is lost when the site is ATGTGT. The C to T polymorphism occurs at position 729 in the 852 bp UTR (FIG 1 and SEQ ID NO:1) and position 1205 in this sequence (FIG. 2 and SEQ ID NO:9). Also shown on this figure are the forward P3' primer (SEQ ID NO:4) and reverse P4' primer (SEQ ID NO:5) used to synthesize the 442 bp probe used in Southern blotting experiments described in Example 1.

FIG. 3 illustrates the diagnostic restriction fragment length polymorphism analysis (RFLP) patterns obtained with the PCR assay described in FIG. 2. The genotypes illustrated are as follows: 1-C/C; 2-C/T; 3-T/T. The sizes of the fragments observed are shown to left of the figure. The 671 bp fragment is common to all genotypes. The pattern shown for the 566 bp and 442 bp fragments is also observed with genomic Southern blots using the 442 bp probe.

DETAILED DESCRIPTION OF THE INVENTION

Based on the frequencies of the C/C, C/T, and T/T germline genotypes at position 729 (as defined in FIG. 1 of the application) in the prohibitin 3'UTR among controls and cancer cases, a simple test has been developed to determine the susceptibility of lifetime probability of an individual developing cancer. The determination of an individual's germline prohibitin genotype with regard to position 729 of the 3'UTR provides a predictor of the individual's probability of developing cancer; that is, whether the individual is homozygous thymine (T/T) or homozygous cytosine (C/C) or heterozygous (C/T) at position 729.

To determine an individual's genotype at position 729, genomic DNA can be isolated from a wide variety of patient samples using standard techniques. Preferably, the genomic DNA is isolated from either blood or buccal cell smears as described in Example 1. Following preparation of genomic DNA, the region containing base 729 of the prohibitin 3'UTR must be amplified, or the genomic DNA may be directly digested (Example 1). Like the preparation of genomic DNA, this too can be done by a wide variety of standard techniques. Preferably, this region is amplified by polymerase chain reaction ("PCR") techniques, as described in Example 1.

Preferably, following PCR amplification, a restriction fragment length polymorphism ("RFLP") analysis is conducted as described in Example 1. This analysis is based on the fact that the ) substitution of a T for C at position 729 in the 3' UTR results in the loss of cleavability by the restriction endonuclease AflIII at its six base recognition site which spans position 729.

Alternatively, the PCR amplified sequence at position 729 could be determined by any other means for distinguishing sequence variants such as by direct sequencing using Ampli-Cycle™ PCR kit (Perkin Elmer) or Southern blotting.

Being able to accurately determine an individual's genotype with respect to position 729 serves a variety of useful purposes. First and foremost, as already described above, it provides a means by which an individual's lifetime probability of developing cancer can be predicted. For those who are diagnosed as having an increased risk, an enhanced awareness of the increased risk in conjunction with more frequent examinations may lead to an earlier detection of the cancer and an increased chance of survival. This would be particularly useful for the newborn to those up to the age of 40 who are generally not yet screened for the development of cancer.

The assay could also be used in genetic counseling. Where the parents are both homozygous for the T-allele (T/T at position 729), the probability of having a child with the T/T genotype is 100%. Conversely, where the parents are both homozygous for the C-allele (C/C at position 729), the probability of having a child with the T/T genotype is 0%. Where only one parent is homozygous for the T-allele, or where one or both parents are heterozygous (C/T at position 729), the probability of having a child with the T/T genotype is somewhere between these two extremes and can be determined according to classic Mendelian genetics. Depending on their genotypes, the parents of a child could then determine the child's genotype as a newborn or even prenatally. This information could then be used as described above to determine an optimum schedule of examinations to ensure early detection and treatment of cancer.

This assay could also be used for cancer prognosis, the prediction of disease-free interval, long-term survivorship, and determination of therapy for both women and men.

Prostate Cancer

Table I presents germline prohibitin genotypes for prostate cancer patients and male controls. The mean age±standard deviation for the control and cases were 41.2±13.6 and 73.9±8.4 years, respectively. The majority of the cases and controls (95%) are Caucasian males residing in Oklahoma. Potential relative risk of prostate cancer was determined in terms of the odds ratio (OR).

TABLE I

Genotype and Allele Frequencies of 3' UTR Variants Among Prostate Cancer Cases and Male Controls[a]

|  | Cases | | Controls | |
|---|---|---|---|---|
|  | Number | Frequency | Number | Frequency |
| Genotype | | | | |
| C/C | 6 | 0.40 | 25 | 0.68 |
| C/T | 7 | 0.47 | 10 | 0.27 |

TABLE I-continued

Genotype and Allele Frequencies of 3' UTR Variants Among Prostate Cancer Cases and Male Controls[a]

| | Cases | | Controls | |
|---|---|---|---|---|
| | Number | Frequency | Number | Frequency |
| T/T | 2 | 0.13 | 2 | 0.05 |
| Total Alleles | 15 | 1.00 | 37 | 1.00 |
| C | 19 | 0.63 | 60 | 0.81 |
| T | 11 | 0.37 | 14 | 0.19 |
| Total | 30 | 1.00 | 74 | 1.00 |

[a]Computed Exact Odds Ratio = 3.05; 95% confidence interval = (0.87–11.27); exact p-value = 0.08.

An estimated odds ratio for subjects having C/T and subjects having T/T combined, i.e., T carrier, was also calculated as $OR_T$=[(number of prostate cancer patients having C/T+number of prostate cancer patients having T/T)×(number of unaffected subjects having C/C)]÷[(number of prostate cancer patients C/C)×(number of unaffected subjects having C/T+number of unaffected subjects having T/T)], i.e., (9×25)÷(6×12)=3.13. While the calculated odds ratios may vary depending on the size of the sampled population, it is expected that the disclosed ratios will provide a useful guide as to risk.

Ovarian Cancer

Table II presents germline-prohibitin genotypes for ovarian cancer patients and female controls. The mean age±standard deviation for the control and cases were 40.0±12.44 and 62.3±13.7 years, respectively. The majority of the cases and controls (95%) are Caucasian females residing in Oklahoma. Potential relative risk of ovarian cancer was also examined in terms of the odds ratio (OR).

An estimated odds ratio for subjects having C/T and subjects having T/T combined, i.e., T carrier, was also calculated as $OR_T$=[(number of ovarian cancer patients having C/T+number of ovarian cancer patients having T/T)×(number of unaffected subjects having C/C)]÷[(number of ovarian cancer patients C/C)×(number of unaffected subjects having C/T+number of unaffected subjects having T/T)], i.e., (7×67)÷(7×29)=2.31. Again, while the calculated odds ratios may vary depending on the size of the sampled population, it is expected that the disclosed ratios will provide a useful guide as to risk.

TABLE II

Genotype and Allele Frequencies of 3' UTR Variants Among Ovarian Cancer Cases and Female Controls[a]

| | Cases | | Controls | |
|---|---|---|---|---|
| | Number | Frequency | Number | Frequency |
| Genotype | | | | |
| C/C | 7 | 0.50 | 67 | 0.70 |
| C/T | 6 | 0.43 | 28 | 0.29 |
| T/T | 1 | 0.07 | 1 | 0.01 |
| Total | 14 | 1.00 | 96 | 1.00 |
| Alleles | | | | |
| C | 20 | 0.71 | 162 | 0.84 |
| T | 8 | 0.29 | 30 | 0.16 |
| Total | 28 | 1.00 | 192 | 1.00 |

[a]Computed Exact Odds Ratio = 2.30; 95% confidence interval = (.71–7.43); exact p-value = 0.14.

A diagnostic assay to determine a patient's germline prohibitin genotype with regard to position 729 of the prohibitin 3' UTR as given in SEQ ID NO:1 may be used to predict a patient's susceptibility to all types of cancer. Candidates for the diagnostic assay include the general population, and more specifically, individuals reporting a family history of cancer. Further, a screening of sequences from tumors or cell lines for changes at position 729 from the wild type prohibitin 3' UTR can also be used to identify individuals for whom the cancer susceptibility assay is appropriate. For example, a patient from whom the glioblastoma cell line designated T98G exhibiting a C→T change at position 729 was derived (Jupe et al. "The 3' untranslated region of prohibitin and cellular immortalization," *Exp Cell Res* 224:128–135 (1996)) would be a candidate for the diagnostic assay for susceptibility to other types of cancer. As another example, the 852 base prohibitin wild type sequence (Genbank Acc. #U49725) was used as a query sequence in a BLASTN search (Altschul, et al., "Basic local alignment search tool," *J Mol Biol* 215: 403–410 (1990)) against the non-redundant database of expressed sequence tags (ESTs). This search identified three ESTs from dissected tumors that were potentially products of the T-allele at position 729 as defined by SEQ ID NO:1 of the prohibitin 3'UTR. These three ESTs are further identified in Table III below. In addition, a sequence from a human carcinoma cell line (T84 in Table III) derived from a lung metastasis of a colon carcinoma is the product of a T-allele that also exhibits additional changes in the 3'UTR. The presence of the T-allele at position 729 in these tumors and cell line indicates a change to the 3'UTR which represents either a somatic mutation or a germline polymorphism. By applying the cancer susceptibility assay of the present invention, the patients from whom these tumors and cell line were derived could be screened to determine the germline prohibitin genotype with regard to position 729 of the prohibitin 3'UTR as given in SEQ ID NO:1. If conclusive identification of a germline polymorphism at position 729 is found, it would then predict the patient's increased susceptibility to all types of cancer.

TABLE III

ESTs with T-allele of the Prohibitin 3' UTR

| # | Accession # | Tissue Source | Date Deposited |
|---|---|---|---|
| 1 | AA284327 | Ovarian tumor | May 15, 1997 |
| 2 | AA578743 | Lung tumor | Sep. 12, 1997 |

TABLE III-continued

ESTs with T-allele of the Prohibitin 3' UTR

| # | Accession # | Tissue Source | Date Deposited |
|---|---|---|---|
| 3 | AA564922 | Adrenal adenoma | Sep. 5, 1997 |
| 4 | AA055656 | T84 cell line | Aug. 1, 1997 |

EXAMPLE 1

Diagnostic Assay Methodology

The diagnostic assay for determining susceptibility of cancer based on the sequence of the 3'UTR of the prohibitin gene is described below. The assay is applicable to all types of cancer.

Sample Collection

Blood samples (approx. 10 ml) were collected by routine venipuncture into tubes containing anticoagulant.

Buccal cell smears were collected using sterile cytology brushes (type H—Histobrush, 174-600; Spectrum Laboratories, Dallas, Tex.). The study participant was instructed to twirl the brush on the inner cheek for 30 seconds on each side. The brush was then inserted into a sterile collection tube, tightly capped, and stored at 4° C. prior to DNA template preparation.

DNA Preparation

The DNA from blood samples was prepared using the PureGene Kit (Gentra, Minneapolis, Minn.).

The DNA from buccal cell smears was isolated using a method described by Horrigan, et al., "Polymerase chain reaction-based diagnosis of Del(5q) in acute myeloid leukemia and myelodysplastic syndrome identifies a minimal deletion interval," *Blood* 88:2665–2670 (1996), which is a modification of a method originally published by Richards, et al., "Multiplex PCR amplification from the CFTR gene using DNA prepared from buccal brushes/swabs," *Hum Mol Genet* 2:159–160 (1993). The cytology brush was transferred to a 1.5 ml tube containing 0.6 ml of 50 mM sterile NaOH. The handle of the brush was clipped, and the lid was closed. After vortexing for 30 seconds, the sample was heated to 95° C. for 5 minutes. The tube was vortexed again, and the brush was drained to recover residual liquid prior to removal from the tube. The solution was neutralized by adding 0.06 ml of 1 mM Tris, pH=8.0. After thorough mixing, the sample was stored at −20° C. The assay can also be performed on high molecular weight DNA purified from skin, hair follicles, and virtually any other tissue source as well as from fibroblast or lymphoblast cell lines. In this case, the DNA can be prepared using the PureGene kit (Gentra, Minneapolis, Minn.), or any similar method, in accordance with the manufacturer's instructions.

Polymerase Chain Reaction

PCR reactions were run on 0.1 µg of genomic DNA purified from blood or 0.010 ml of buccal smear extract using Taq Gold polymerase (Perkin Elmer, Foster City, Calif.). The reaction conditions used were as follows: 10 mM Tris-HCl, pH=8.0, 50 mM KCl, 1.5 mM MgCl, 100–200 µM each of dATP, dGTP, dTTP, and dCTP, 0.1% Triton X-100, 0.5–1.0 units Taq Gold polymerase, and 100 ng of each primer in a 50-µl reaction mix.

In one form of the assay, as illustrated in FIG. 1 and SEQ ID NO:1, an 852 bp 3'UTR synthesized with primers 5'-CCCAGAAATCACTGTG-3' (primer P1, sense) (SEQ ID NO:6) and primer P2 (SEQ ID NO:2) is gel purified and a secondary PCR product is synthesized using the primers 5'-TGAGTCCTGTTGAAGACTTCC-3' (primer P3, sense) (SEQ ID NO:7) and 5'-GGAAGGTCTGGGTGTCATTT-3' (primer P2, antisense)(SEQ ID NO:2).

Restriction Fragment Length Polymorphism Analyses

The PCR products were digested with the restriction enzyme AflIII using the buffer and conditions recommended by the manufacturer (New England Biolabs, Cambridge, Mass.). All digestions for a group of individual samples were performed using a diluted master mix. Controls with confirmed sequence were included with each series of digests. The digestion products were separated by electrophoresis on 20% polyacrylamide gels, stained with ethidium bromide and visualized by ultraviolet light.

Alternatively, high molecular weight DNAs purified by using the PureGene kit were analyzed for restriction fragment length polymorphisms by Southern blotting. Generally, 10–15 µg of DNA was digested with the restriction enzyme AflIII (New England Biolabs) at 37° C. for 16 hours using the manufacturer supplied buffer. The digests were terminated by precipitating the DNA by adding 1/10 volume 3M sodium acetate and 2 volumes of absolute ethanol. Following resuspension in water and addition of loading dye (Promega 6X), the samples were loaded into a 1% agarose gel, and electrophoresis was performed until the bromophenol blue loading dye reached the bottom of the gel. Gels were then denatured in 0.5 M NaOH/1.5M NaCl for 30 minutes followed by neutralization in 0.5M Tris/1.5 M NaCl (pH=7.0). A Southern blot was then carried out by capillary transfer to Hybond membrane (Amersham, Arlington Heights, Ill.). The DNA was fixed to the membrane either by baking at 80° C. or crosslinking with ultraviolet light.

The RFLP was detected by probing with a nucleic acid fragment containing the prohibitin 3'UTR. The routinely used probe was a 442 bp nucleic acid fragment that lies immediately 5' to the polymorphic AflIII cut site. It was synthesized by PCR using a full length 3'UTR clone for template and primers P3' and P4' (FIG. 2). The probe was labeled using a random primer labeling kit (Pharmacia, Piscataway, N.J.). The membranes were hybridized at least 12 hours at 65° C. and washed at the same temperature under high stringency. The filter was then exposed to x-ray film or a phosphoimager screen to display the RFLP for interpretation. Alternatively, a 124 bp fragment 3' to the polymorphic AflIII site, as well as the 566 bp fragment synthesized with P3' and P2 primers (FIG. 2) may be used as a probe. Any of these probes will display an RFLP that distinguishes the different genotypes. Southern blots probed with the 442 bp probe displayed the 566 bp and 442 bp banding pattern shown in FIG. 3.

The substitution of a T for C at position 729 (FIG. 1) in the 3'UTR results in the loss of cleavability by AflIII at its six base recognition sequence. Our analyses of mutated tumors, cancer cell lines, and buccal cell scrapes from homozygous T cancer patients show that the C to T at 729 is the only change in the recognition site thus far detected that is responsible for loss of AflIII cutting. Homozygous C individuals have both alleles cut at the polymorphic site, while alleles of homozygous T individuals do not cut. Heterozygous individuals have one allele of each, C and T.

EXAMPLE 2

Alternative Diagnostic Assay Method

An alternative assay was performed as given in Example 1, with the exception that the secondary PCR product was synthesized using the sense primer P4, 5'-GGATGGACT-TGTATAG-3' (SEQ ID NO:8) and the antisense primer 5'-GGAAGGTCTGGGTGTCATTT-3' (primer P2, antisense)(SEQ ID NO:2).

EXAMPLE 3

Alternative Diagnostic Assay Method

An alternative assay was performed as given in Example 1, with the exception that, as illustrated in the 1237 bp genomic sequence given in FIG. 2 and SEQ ID NO:9, the primers utilized were 5'-AAGGTGGCTTTCTGGTGAAG-3' (primer P1', sense) (SEQ ID NO:3) and 5'-GGAAG-GTCTGGGTGTCATTT-3' (primer P2, antisense)(SEQ ID NO:2). In this assay using SEQ ID NO:9, the base at position 1205 corresponds to the position 729 in SEQ ID NO:1.

FIG. 3 illustrates the pattern of bands produced in this assay for each genotype. Utilizing the sense primer SEQ ID NO:3 and antisense primer SEQ ID NO:2, the RFLP pattern for a homozygous C individual (C/C) shows that for both DNA strands, the 566 bp measured from the constitutive AflIII site to the end of the 3'UTR was cut at position 729/1205 into two distinct bands of 442 bp and 124 bp. A homozygous T individual (T/T) produced one band of 566 bp measured from the constitutive AflIII site to the end of the 3'UTR which was uncut at position 729/1205 on both DNA strands. The heterozygous individual (C/T) gave three distinct bands, showing that for one DNA strand, the 566 bp measured from the constitutive AflIII site to the end of the 3'UTR was cut at position 729/1205 into two distinct bands of 442 bp and 124 bp, and for the other DNA strand, one band of 566 bp measured from the constitutive AflIII site to the end of the 3'UTR was uncut at position 729/1205. In this assay, a band common to all genotypes is the 671 bp fragment measured from the 5' end of the PCR product to the constitutive cut site.

This method requires a single PCR reaction and AflIII digestion, and shows 100% correlation with Southern blot results.

EXAMPLE 4

Alternative Approaches

The predictive value of this assay involves determining the germline genotype of an individual at position 729 in the prohibitin 3'UTR. There are many potential specific methods that can be used to accomplish this task. We have primarily used the RFLP described in Example 1 and DNA sequencing to collect our data. However, any other methods based on single base oligonucleotide mismatch screening (Jupe, E. R. and Zimmer, E. A., "Assaying differential ribosomal RNA gene expression with allele-specific oligonucleotide probes," In *Methods in Enzymology-Molecular Evolution: Producing the Biochemical Data*, Academic Press, pp. 541–552, 1993), allele specific PCR amplification (Allen, et al., *BioTechniques* 19:454 (1995); Ault, G., *J Virological Methods* 46:145–156 (1994); Tada, M., *Cancer Research* 53:2472–2474 (1993); Huang, *Nucleic Acids Research* 20:4567–4573 (1992); Sommer, *BioTechniques* 12:82–87 (1992); and Kwok, *Nucleic Acids Research* 18:999–1005 (1990)), or a method employing a high specificity thermostable ligase (Ampligase, Epicenter Technologies) could be applied for detection of the polymorphism. In addition, any method currently in use such as single strand conformation polymorphisms or denaturing gradient gel electrophoresis, or any method developed in the future for detecting single base changes, could also be applied to the detection of these genotypes. This test could also be performed starting with RNA and using any of a variety of techniques currently in use or any method developed in the future for detecting single base changes. For example, the RNA would be analyzed directly by sequencing or converted to cDNA using reverse transcriptase (Castles, et al., *BioTechniques* 21:425–428 (1996), followed by PCR and any method capable of detecting single base changes.

EXAMPLE 5

Diagnostic Assay for Cancer Susceptibility

Identifying a patient's germline prohibitin genotype as homozygous thymine (T/T), homozygous cytosine (C/C), or heterozygous (C/T) at position 729 as defined in SEQ ID NO:1 can be used to evaluate a person's risk of developing some form of cancer.

Using the methodologies provided in Example 1–4, a patient's genomic DNA is prepared and amplified via PCR, and the base identity at position 729 is determined by various means known in the art including but not limited to sequencing, RFLP, or size differentiation.

A patient with a germline prohibitin genotype of homozygous thymine (T/T) at position 729 has a greater risk factor of developing cancer than an unaffected relevant population. A patient who is homozygous cytosine (C/C) at position 729 has a risk factor less than or equal to an unaffected relevant population. Finally, a patient who is heterozygous cytosine/thymine (C/T) at position 729 has a risk factor less than an individual homozygous thymine (T/T) but more than an unaffected relevant population.

We claim:

1. A method for determining risk of cancer other than breast cancer comprising the steps of:
   a) determining the base identity of a portion of genomic DNA from a patient cell sample, said genomic DNA comprising a prohibitin gene comprising a 3' untranslated region, said portion corresponding to position 729 as defined in SEQ ID NO:1 of said prohibitin gene in said untranslated region; and
   b) correlating said base identity at position 729 as defined in SEQ ID NO:1 of said genomic DNA with germline polymorphisms at position 729 indicative of a risk for said cancer.

2. The method of claim 1, wherein the base identity of position 729 as defined in SEQ ID NO:1 is determined by sequencing a portion of said portion of 3' untranslated region of said prohibitin gene containing said position 729 as defined in SEQ ID NO:1.

3. The method of claim 1, wherein base identity of said position 729 as defined in SEQ ID NO:1 is determined by detection of single base matches or mismatches between said portion of 3' untranslated region and C-allele and/or T-allele prohibitin.

4. The method of claim 1, wherein the base identity of position 729 as defined in SEQ ID NO:1 is determined by digesting said portion of 3' untranslated region of said prohibitin gene with a restriction endonuclease appropriate to determine the base identity of said position 729 as defined in SEQ ID NO:1.

5. The method of claim 4, wherein said restriction endonuclease is AflIII, and whereby it is determined that a cleavage site affected by AflIII is present when position 729 as defined in SEQ ID NO:1 is cytosine.

6. The method of claim 5, further comprising the steps of:
   a) separating said digested portion of 3' untranslated region DNA strands;
   b) fixing said separated digested 3' untranslated region DNA strands onto a membrane;
   c) hybridizing said separated digested 3' untranslated region DNA strands with at least one labeled nucleic acid probe, wherein said labeled nucleic acid probe can complementarily bind to said fixed separated digested 3' untranslated region DNA strands and can identify whether cleavage at said position 729 as defined in SEQ ID NO:1 occurred; and
   d) detecting if said labeled nucleic acid probe has bound to said fixed separated digested 3' untranslated region DNA strands, wherein said patient is at risk for cancer if said labeled nucleic acid probe bound to said fixed separated digested 3' untranslated region DNA strands indicates cleavage at said position 729 as defined in SEQ ID NO:1 did not occur.

7. The method of claim 1, wherein said base identity is determined by examining an RNA fraction from said patient cell sample, whereby the identity of said genomic DNA at said position 729 as defined in SEQ ID NO:1 can be determined.

8. The method of claim 1, wherein a lifetime risk for developing cancer is assessed to be greater than that of the unaffected relevant population when the base identity at said position 729 as defined in SEQ ID NO:1 is homozygous for thymine.

9. The method of claim 1, wherein a lifetime risk for developing cancer is assessed to be greater than that of the unaffected relevant population but less than that of an individual who is homozygous for thymine when the base identity at said position 729 as defined in SEQ ID NO:1 is heterozygous cytosine/thymine.

10. The method of claim 1, wherein a lifetime risk for developing cancer is assessed to be less than or equal to the unaffected relevant population when the base identity at said position 729 as defined in SEQ ID NO:1 is homozygous cytosine.

11. The method of claim 1, wherein said portion of genomic DNA comprises synthesized double-stranded genomic DNA obtained by polymerase chain reaction methodology comprising the steps of:
   a) isolating a portion of double-stranded genomic DNA from a patient cell sample, said genomic DNA comprising a prohibitin gene comprising a 3' untranslated region;
   b) separating said double-stranded genomic DNA into a first single-stranded genomic DNA and a second single-stranded genomic DNA in a first reaction zone;
   c) providing a sense primer to said reaction zone, said reaction zone having conditions favorable for hybridization between said first single-stranded genomic DNA and said sense primer;
   d) simultaneously providing an antisense primer to said reaction zone, said reaction zone having conditions favorable for hybridization between said second single-stranded genomic DNA and said antisense primer;
   e) making multiple copies of said portion of double-stranded genomic DNA by polymerase chain reaction methodology to form synthesized double-stranded DNA;
   f) determining the base identity of position 729 as defined by SEQ ID NO:1 for said 3' untranslated region DNA strands; and
   g) correlating said base identity with a germline polymorphism indicative of a risk for said cancer, wherein said patient is at lowest risk with homozygous C/C, intermediate risk with heterozygous C/T, and greatest risk with homozygous T/T at said position 729.

12. The method of claim 11, wherein said sense primer comprises SEQ ID NO:7.

13. The method of claim 11, wherein said sense primer comprises SEQ ID NO:6.

14. The method of claim 11, wherein said sense primer comprises SEQ ID NO:8.

15. The method of claim 11, wherein said sense primer comprises SEQ ID NO:3.

16. The method of claim 11, wherein said antisense primer comprises SEQ ID NO:2.

17. The method of claim 12, wherein said antisense primer comprises SEQ ID NO:2.

18. The method of claim 13, wherein said antisense primer comprises SEQ ID NO:2.

19. The method of claim 14, wherein said antisense primer comprises SEQ ID NO:2.

20. The method of claim 15, wherein said antisense primer comprises SEQ ID NO:2.

21. The method of claim 18, further comprising, prior to step f, purifying an 852 bp fragment and performing secondary polymerase chain reaction using sense primer comprising SEQ ID NO:7 and antisense primer comprising SEQ ID NO:2 to form synthesized double-stranded DNA.

22. The method of claim 11, wherein base identity of said position 729 as defined in SEQ ID NO:1 is determined by sequencing.

23. The method of claim 11, wherein base identity of said position 729 as defined in SEQ ID NO:1 is determined by detection of single base matches or mismatches between said synthesized double-stranded DNA and C-allele and/or T-allele prohibitin.

24. The method of claim 11, wherein base identity of said position 729 as defined in SEQ ID NO:1 is determined by restriction fragment length polymorphism.

25. The method of claim 11 further comprising digesting said synthesized double-stranded DNA with restriction endonuclease AflIII which cleaves said untranslated region at said base 729 as defined in SEQ ID NO:1 when said base is cytosine.

26. The method of claim 21 further comprising digesting said synthesized double-stranded DNA with restriction endonuclease AflIII which cleaves said untranslated region at said base 729 as defined in SEQ ID NO:1 when said base is cytosine.

27. The method of claim 25, further comprising the steps of:
   h) separating said digested synthesized double-stranded DNA strands;
   i) fixing said separated digested synthesized double-stranded DNA strands onto a membrane;
   j) hybridizing said separated digested synthesized double-stranded DNA strands with at least one labeled nucleic acid probe, wherein said labeled nucleic acid probe can complementarily bind to said fixed separated digested synthesized double-stranded DNA strands and can identify whether cleavage at said position 729 as defined in SEQ ID NO:1 occurred; and
   k) detecting if said labeled nucleic acid probe has bound to said fixed separated digested synthesized double-stranded DNA strands, wherein said patient is at risk for cancer if said labeled nucleic acid probe bound to said fixed separated digested synthesized double-stranded DNA strands indicates cleavage at said position 729 as defined in SEQ ID NO:1 did not occur.

28. The method of claim 25, further comprising the steps of:
   h) separating said digested synthesized double-stranded DNA strands; and
   i) visualizing said digested synthesized double-stranded DNA fragment pattern by ethidium bromide staining and ultraviolet photography.

29. The method of claim 26 further comprising the steps of:
   h) separating said digested synthesized double-stranded DNA strands;
   i) fixing said separated digested synthesized double-stranded DNA strands onto a membrane;
   j) hybridizing said separated digested synthesized double-stranded DNA strands with at least one labeled nucleic acid probe, wherein said labeled nucleic acid probe can complementarily bind to said fixed separated digested synthesized double-stranded DNA strands and can identify whether cleavage at said position 729 as defined in SEQ ID NO:1 occurred; and
   k) detecting if said labeled nucleic acid probe has bound to said fixed separated digested synthesized double-stranded DNA strands, wherein said patient is at risk for cancer if said labeled nucleic acid probe bound to said fixed separated digested synthesized double-stranded DNA strands indicates cleavage at said position 729 as defined in SEQ ID NO:1 did not occur.

30. The method of claim 26, further comprising the steps of:
   h) separating said digested synthesized double-stranded DNA strands; and
   i) visualizing said digested synthesized double-stranded DNA fragment pattern by ethidium bromide staining and ultraviolet photography.

31. The method of claim claim 1, wherein said portion of genomic DNA is SEQ ID NO:9.

32. The method of claim 1, wherein said sense primer SEQ ID NO:3 is used to amplify SEQ ID NO:9.

33. The method of claim 1, wherein said antisense primer SEQ ID NO:2 is used to amplify SEQ ID NO:9.

34. The method of claim 32, wherein said antisense primer SEQ ID NO:2 is used to amplify SEQ ID NO:9.

35. The method of claim 34, wherein base identity of said position 729 as defined in SEQ ID NO:1 is determined by sequencing.

36. The method of claim 34, wherein base identity of said position 729 as defined in SEQ ID NO:1 is determined by detection of single base mismatches between said synthesized double-strand DNA and C-allele and/or T-allele prohibitin.

37. The method of claim 34, wherein base identity of said position 729 as defined in SEQ ID NO:1 is determined by restriction fragment length polymorphism.

38. The method of claim 34 further comprising digesting said synthesized double-stranded DNA with restriction endonuclease AflIII which cleaves said untranslated region at said base 729 as defined in SEQ ID NO:1 when said base is cytosine.

39. The method of claim 38, further comprising the steps of:
  h) separating said digested synthesized double-stranded DNA strands;
  i) fixing said separated digested synthesized double-stranded DNA strands onto a membrane;
  j) hybridizing said separated digested synthesized double-stranded DNA strands with at least one labeled nucleic acid probe, wherein said labeled nucleic acid probe can complementarily bind to said fixed separated digested synthesized double-stranded DNA strands and can identify whether cleavage at said position 729 as defined in SEQ ID NO:1 occurred; and
  k) detecting if said labeled nucleic acid probe has bound to said fixed separated digested synthesized double-stranded DNA strands, wherein said patient is at risk for cancer if said labeled nucleic acid probe bound to said fixed separated digested synthesized double-stranded DNA strands indicates cleavage at said position 729 as defined in SEQ ID NO:1 did not occur.

40. The method of claim 38, further comprising the steps of:
  h) separating said digested synthesized double-stranded DNA strands; and
  i) visualizing said digested synthesized double-stranded DNA fragment pattern by ethidium bromide staining and ultraviolet photography.

41. A method for determining the risk for cancer other than breast cancer in a human patient, comprising the steps of:
  a) determining the sequence of RNA isolated from said patient in a region which is a transcription of a portion of genomic DNA, said genomic DNA comprising a prohibitin gene comprising a 3' untranslated region, said portion corresponding to position 729 as defined in SEQ ID NO:1 of said prohibitin gene in said untranslated region; and
  b) correlating said base identity at position 729 as defined in SEQ ID NO:1 of said genomic DNA with germline polymorphisms at position 729 indicative of a risk for said cancer.

* * * * *

UNITED STATES PATENT AND TRADEMARK OFFICE
CERTIFICATE OF CORRECTION

| | | |
|---|---|---|
| PATENT NO. | : 7,094,538 B2 | Page 1 of 1 |
| APPLICATION NO. | : 10/166218 | |
| DATED | : August 22, 2006 | |
| INVENTOR(S) | : Jupe et al. | |

It is certified that error appears in the above-identified patent and that said Letters Patent is hereby corrected as shown below:

In claim 31, column 18, line 64, delete "claim 1" and insert -- claim 11 -- therefor.

In claim 32, column 18, line 66, delete "claim 1" and insert -- claim 31 -- therefor.

In claim 33, column 19, line 1, delete "claim 1" and insert -- claim 31 -- therefor.

Signed and Sealed this

Tenth Day of July, 2007

JON W. DUDAS
*Director of the United States Patent and Trademark Office*

SEQUENCE LISTING

<160> NUMBER OF SEQ ID NOS: 9

<210> SEQ ID NO 1
<211> LENGTH: 852
<212> TYPE: DNA

<213> ORGANISM: Homo sapiens

<400> SEQUENCE: 1

```
cccagaaatc actgtgaaat ttcatgattg gcttaaagtg aaggaaataa aggtaaaatc      60
acttcagatc tctaattagt ctatcaaatg aaactctttc attcttctca catccatcta     120
cttttttatc cacctcccta ccaaaaattg ccaagtgcct atgcaaacca gctttaggtc     180
ccaattcggg gcctgctgga gttccggcct gggcaccagc atttggcagc acgcaggcgg     240
ggcagtatgt gatggactgg ggagcacagg tgtctgccta gatccacgtg tggcctccgt     300
cctgtcactg atggaaggtt tgcggatgag ggcatgtgcg gctgaactga gaaggcaggc     360
ctccgtcttc ccagcggttc ctgtgcagat gctgctgaag agaggtgccg gggaggggca     420
gagaggaagt ggtctgtctg ttaccataag tctgattctc tttaactgtg tgaccagcgg     480
aaacaggtgt gtgtgaactg ggcacagatt gaagaatctg ccctgttga ggtgggtggg      540
cctgactgtt gccccccagg gtcctaaaac ttggatggac ttgtatagtg agagaggagg     600
cctggaccga gatgtgagtc ctgttgaaga cttcctctct acccccacc ttggtccctc      660
tcagataccc agtggaattc caacttgaag gattgcatcc tgctggggct gaacatgcct     720
gccaaagacg tgtccgacct acgttcctgg cccctcgtt cagagactgc ccttctcacg      780
ggctctatgc ctgcactggg aaggaaacaa atgtgtataa actgctgtca ataaatgaca     840
cccagacctt cc                                                         852
```

<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: Complement((1)..(20))
<223> OTHER INFORMATION: DNA primer; antisense

<400> SEQUENCE: 2

```
ggaaggtctg ggtgtcattt                                                  20
```

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: DNA primer

<400> SEQUENCE: 3

```
aaggtggctt tctggtgaag                                                  20
```

<210> SEQ ID NO 4
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: DNA primer

<400> SEQUENCE: 4

```
ggcctccgtc ctgtcactg                                                   19
```

<210> SEQ ID NO 5
<211> LENGTH: 20

```
<212> TYPE: DNA
<213> ORGANISM: Homo sapiens
<220> FEATURE:
<221> NAME/KEY: misc_feature
<222> LOCATION: (1)..(20)
<223> OTHER INFORMATION: DNA primer

<400> SEQUENCE: 5
ctttggcagg catgttcagc                                                     20

<210> SEQ ID NO 6
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: DNA primer

<400> SEQUENCE: 6
cccagaaatc actgtg                                                         16

<210> SEQ ID NO 7
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: DNA primer

<400> SEQUENCE: 7
tgagtcctgt tgaagacttc c                                                   21

<210> SEQ ID NO 8
<211> LENGTH: 16
<212> TYPE: DNA
<213> ORGANISM: Homo sapiens
<220> FEATURE:
<221> NAME/KEY: misc_feature
<222> LOCATION: (1)..(16)
<223> OTHER INFORMATION: DNA primer

<400> SEQUENCE: 8
ggatggactt gtatag                                                         16

<210> SEQ ID NO 9
<211> LENGTH: 1328
<212> TYPE: DNA
<213> ORGANISM: Homo sapiens
<220> FEATURE:
<221> NAME/KEY: 5'clip
<222> LOCATION: (1)..(477)

<400> SEQUENCE: 9
aggactggtg ggcaatgtgc tctgcttccc cccgcttccc ccgctagcca tcaggaggaa         60
gtaaactccc cgagttcctt caggagcctg ggaaggtggc tttctggtga agggcctttg        120
gttgtagcct gacatgcggt gccctgaggt ttgatctttg tctccacctc cattctttta        180
ggctgagcaa cagaaaaagg cggccatcat ctctgctgag ggcgactcca aggcagctga        240
gctgattgcc aactcactgg ccactgcagg ggatggcctg atcgagctgc gcaagctgga        300
agctgcagag gacatcgcgt accagctctc acgctctcgg aacatcacct acctgccagc        360
ggggcagtcc gtgctcctcc agctgcccca gtgagggccc accctgcctg cacctccgcg        420
ggctgactgg gccacagccc cgatgattct taacacagcc ttccttctgc tcccacccca        480
```

```
gaaatcactg tgaaatttca tgattggctt aaagtgaagg aaataaaggt aaaatcactt      540
cagatctcta attagtctat caaatgaaac tctttcattc ttctcacatc catctacttt      600
tttatccacc tccctaccaa aaattgccaa gtgcctatgc aaaccagctt taggtcccaa      660 ttcgggcct gctggagttc cggcctgggc accagcattt ggcagcacgc aggcggggca       720
gtatgtgatg gactggggag cacaggtgtc tgcctagatc cacgtgtggc ctccgtcctg      780
tcactgatgg aaggtttgcg gatgagggca tgtgcggctg aactgagaag gcaggcctcc      840
gtcttcccag cggttcctgt gcagatgctg ctgaagagag gtgccgggga ggggcagaga      900
ggaagtggtc tgtctgttac cataagtctg attctcttta actgtgtgac cagcggaaac      960
aggtgtgtgt gaactgggca cagattgaag aatctgcccc tgttgaggtg ggtgggcctg     1020
actgttgccc cccagggtcc taaaacttgg atggacttgt atagtgagag aggaggcctg     1080
gaccgagatg tgagtcctgt tgaagacttc ctctctaccc cccaccttgg tccctctcag     1140
atacccagtg gaattccaac ttgaaggatt gcatcctgct ggggctgaac atgcctgcca     1200
aagacgtgtc cgacctacgt tcctggcccc ctcgttcaga gactgccctt ctcacgggct     1260
ctatgcctgc actgggaagg aaacaaatgt gtataaactg ctgtcaataa atgacaccca     1320
gaccttcc                                                              1328
```